US 6,658,302 B1

(12) United States Patent
Kuzma et al.

(10) Patent No.: US 6,658,302 B1
(45) Date of Patent: Dec. 2, 2003

(54) INSERTION NEEDLE FOR USE WITH IMPLANTABLE, EXPANDABLE, MULTICONTACT ELECTRODES

(75) Inventors: Janusz A. Kuzma, Parker, CO (US); Carla M. Mann, Los Angeles, CA (US)

(73) Assignee: Advanced Bionics Corporation, Sylmar, CA (US)

( * ) Notice: Subject to any disclaimer, the term of this patent is extended or adjusted under 35 U.S.C. 154(b) by 0 days.

(21) Appl. No.: 10/188,168

(22) Filed: Jul. 1, 2002

Related U.S. Application Data

(62) Division of application No. 09/778,267, filed on Feb. 7, 2001, now Pat. No. 6,415,187, which is a continuation of application No. 09/239,927, filed on Jan. 28, 1999, now Pat. No. 6,205,361.
(60) Provisional application No. 60/074,198, filed on Feb. 10, 1998.

(51) Int. Cl.[7] ............................................. A61N 1/05
(52) U.S. Cl. ..................................... 607/116; 607/117
(58) Field of Search ............................. 607/119, 129, 607/115–117, 122; 600/372–374, 377, 381

(56) References Cited

U.S. PATENT DOCUMENTS

| 4,141,365 A | 2/1979 | Fischell et al. ............. 128/404 |
| 4,379,462 A | 4/1983 | Borkan et al. ............. 128/786 |
| 4,989,617 A | 2/1991 | Memberg et al. ............. 128/785 |
| 5,143,067 A | 9/1992 | Rise et al. .................... 128/642 |
| 5,282,468 A | 2/1994 | Klepinski .................... 128/642 |
| 5,391,200 A | * 2/1995 | KenKnight et al. ......... 607/129 |
| 5,443,492 A | * 8/1995 | Stokes et al. ............... 607/131 |
| 5,458,629 A | 10/1995 | Baudino et al. ............ 607/116 |
| 5,611,345 A | * 3/1997 | Hibbeln .................. 128/662.05 |
| 5,634,462 A | 6/1997 | Tyler et al. .................. 128/642 |
| 5,643,330 A | 7/1997 | Holsheimer et al. .......... 607/46 |
| 5,733,322 A | 3/1998 | Starkebaum ................. 607/117 |
| 5,762,629 A | 6/1998 | Kambiri ..................... 604/164 |

FOREIGN PATENT DOCUMENTS

EP 1048271 A2 * 2/2000 ........... A61B/17/34

* cited by examiner

Primary Examiner—Carl Layno
(74) Attorney, Agent, or Firm—Bryant R. Gold

(57) ABSTRACT

An insertion needle facilitates the implantation of an electrode array carried on a flexible, foldable or compressible, subcarrier or substrate. Such subcarrier or substrate folds or compresses during implantation, thereby facilitating its insertion using the insertion needle. Once implanted, such subcarrier or substrate expands, thereby placing the electrodes in a desired spaced-apart positional relationship, and thus achieving a desired electrode array configuration. The insertion needle has a lumen with a non-circular cross-sectional shape, e.g., having a width greater than its height, to facilitate sliding the folded or compressed paddle-type electrode array therein, and further includes a longitudinal slit.

14 Claims, 7 Drawing Sheets

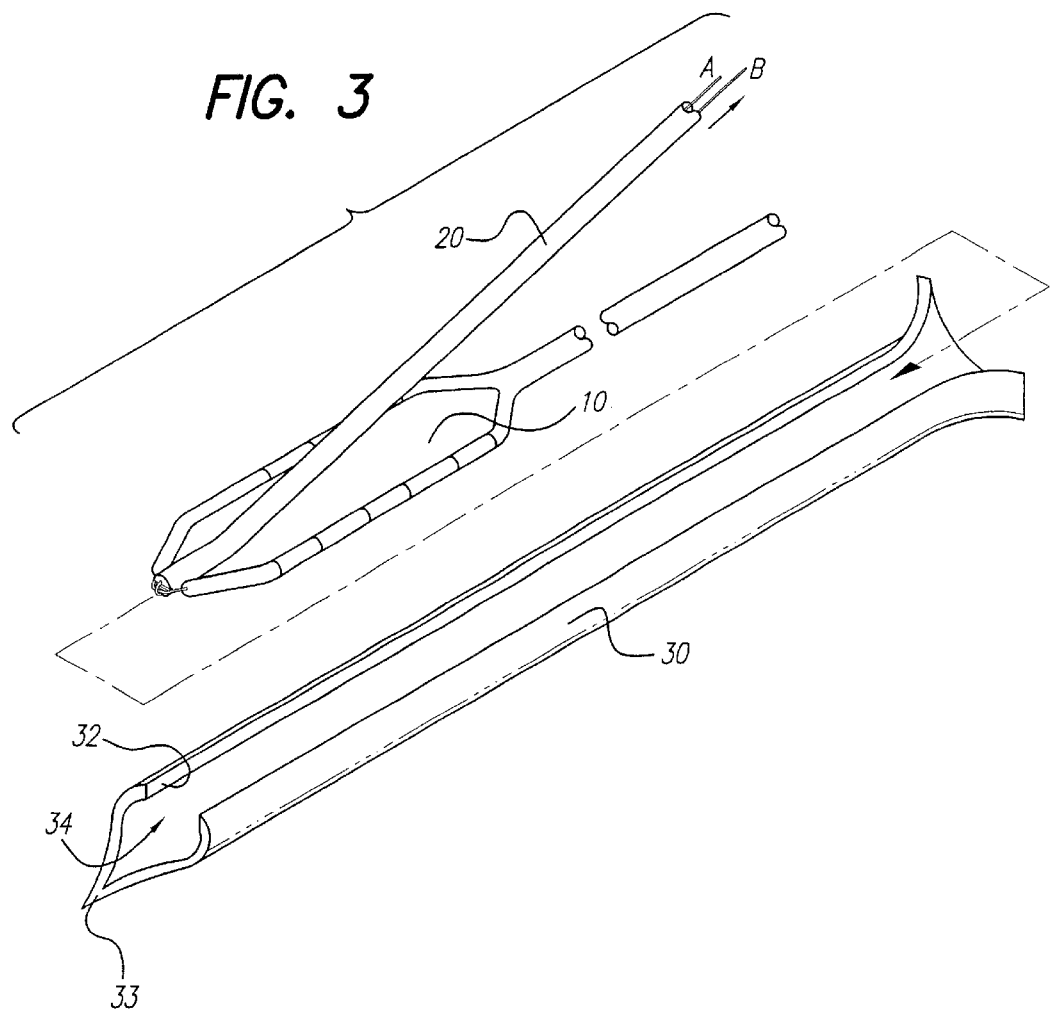

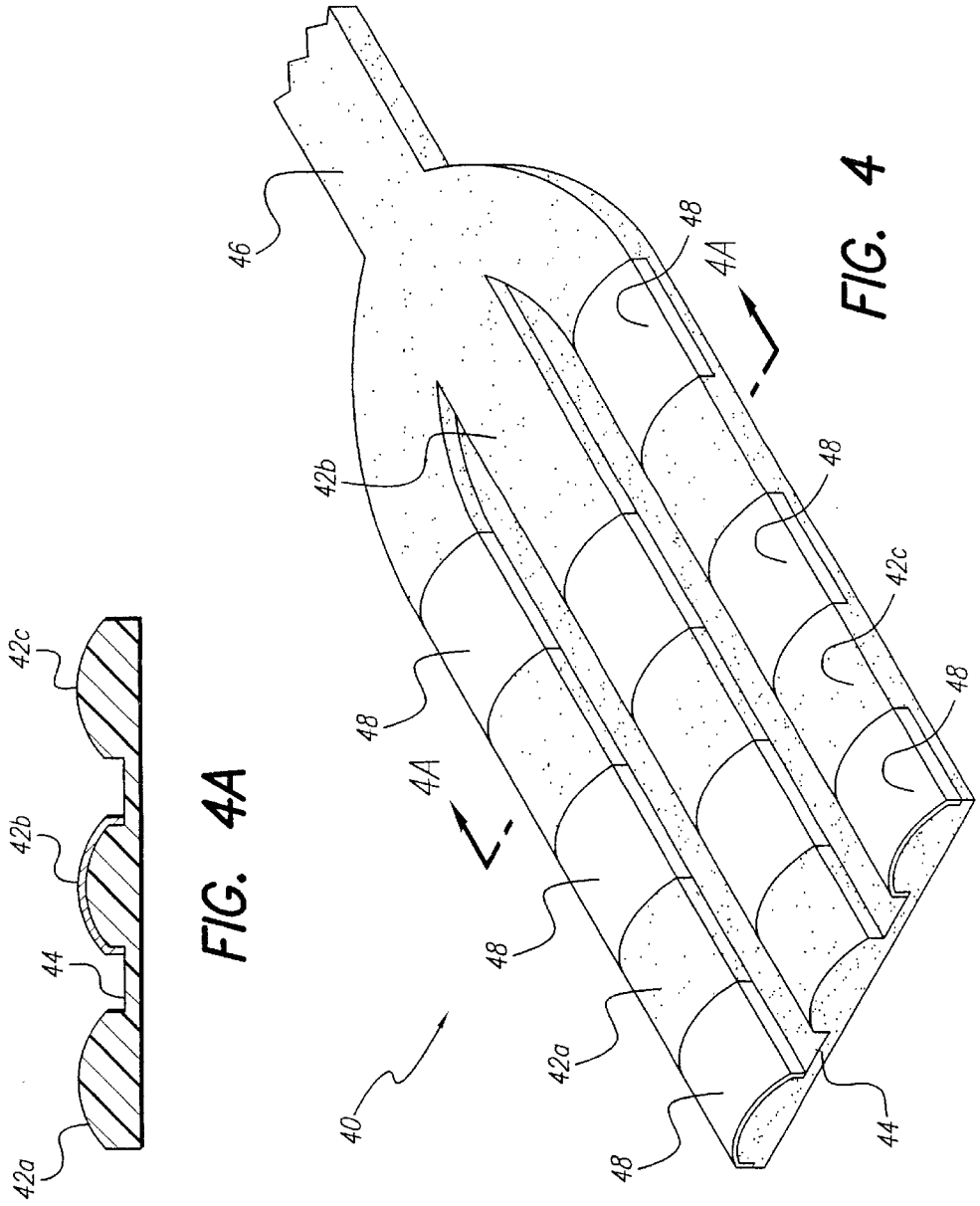

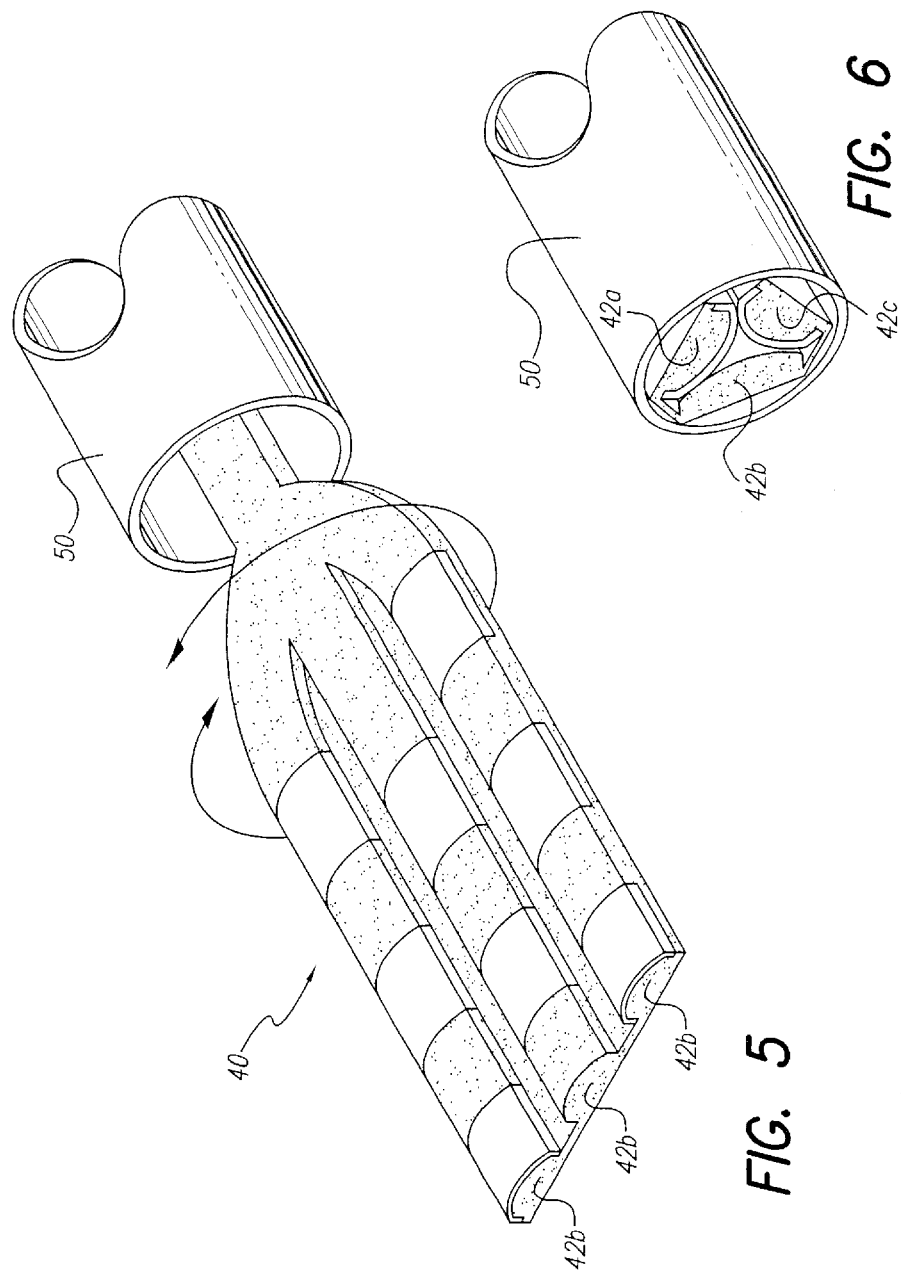

INSERTION NEEDLE FOR USE WITH IMPLANTABLE, EXPANDABLE, MULTICONTACT ELECTRODES

This application is a Divisional of U.S. application Ser. No. 09/778,267, filed Feb. 7, 2001, to be issued as U.S. Pat. No. 6,415,187; which is a Continuation of U.S. application Ser. No. 09/239,927, filed Jan. 28, 1999, now U.S. Pat. No. 6,205,361, which claims the benefit of U.S. Provisional Application Serial No. 60/074,198, filed Feb. 10, 1998.

BACKGROUND OF THE INVENTION

The present invention relates to implantable, expandable, multicontact electrodes. In a preferred embodiment, such electrodes comprise deployable, paddle-type, multicontact electrodes useful for spinal stimulation.

There are two major types of electrodes used for spinal stimulation: (1) percutaneously implanted in-line electrodes/leads requiring local anesthesia for implant, and (2) paddle-shaped electrodes requiring major surgery for implantation.

The first type of electrodes, i.e., the in-line electrodes, comprise thin, rod-type electrodes. Such in-line or rod-type electrodes are easy and less invasive to implant, typically requiring only local anesthesia and the use of a large gauge needle. Disadvantageously, such in-line electrodes are not as stable as paddle leads, and are prone to migration.

The second type of electrodes, i.e., the paddle-shaped electrodes, provide a large-area electrode surface to contact the body tissue, much like a miniature ping-pong paddle. Advantageously, such paddle-type electrodes are more effective and stable than in-line electrodes. Moreover, such paddle-type electrodes provide a platform for multiple electrodes in many possible configurations to thereby optimize electrode programming and clinical results. In contrast, the percutaneous in-line electrodes can only combine electrodes in a vertical row. Disadvantageously, however, the paddle-type electrodes require complex major surgery for implantation, along with all the attendant risks associated with major complex surgery.

It is thus evident, that there is a need in the art for an electrode which can deliver the maximum advantages of the paddle-type electrodes, but without requiring extensive surgery for implantation.

SUMMARY OF THE INVENTION

The present invention addresses the above and other needs by combining the advantages of both the paddle-type electrode and the in-line (rod-type) electrode. That is, the present invention provides an implantable electrode or electrode array that may be implanted like a percutaneously inserted lead, i.e., without requiring major surgery, but once inserted, expands to provide a platform for many electrode configurations.

In accordance with one important aspect of the invention, an electrode array is provided on a flexible, foldable, subcarrier or substrate. Such subcarrier or substrate is folded, or compressed, during implantation, thereby facilitating its insertion using percutaneous implantation techniques. Once implanted, such subcarrier or substrate expands, thereby placing the electrodes in a desired spaced-apart positional relationship, and thus achieving a desired electrode array configuration.

In accordance with another aspect of the invention, the substrate or subcarrier of the electrode array includes a memory element which causes the electrode array to expand or unfold to a desired configuration after the electrode array has been implanted while in a folded up or compressed state.

In accordance with yet another aspect of the invention, the electrode array includes a membrane as an integral part thereof that prevents ingrowth of tissue inside the electrode array, thereby facilitating repositioning, removal, and/or reinsertion of the electrode array, as required.

In one embodiment, the invention may be characterized as a system for implanting an expandable electrode array. Such system includes an electrode array and an insertion tool. The electrode array comprises (a) a flexible substrate, (b) a plurality of parallel columns of spaced-apart electrodes integrally formed on a surface of the flexible substrate, and (c) means for making electrical contact with each electrode in each of the plurality of parallel columns of electrodes. The flexible substrate normally assumes a planar flat shape, but is configured so that it may be collapsed or folded so as to assume a folded or compressed state. The insertion tool comprises a hollow tube or hollow needle wherein the electrode array may be placed while in its folded or compressed state.

In order to implant the electrode array, the hollow tube or needle (with the folded or compressed electrode array therein) is injected into the living tissue of the desired implant site. The folded electrode array is then expelled from the hollow tube and allowed to assume its expanded or unfolded state within the tissue.

It is thus a feature of the present invention to provide a foldable, paddle-type electrode which can be implanted using a simple, needle-type tool without major surgical intervention.

It is a further feature of the invention to provide a loading tool that assists with the folding and inserting of the paddle-type electrode into an insertion tool.

It is yet another feature of the invention to provide a simple method of implanting a foldable, paddle-type electrode that does not require major surgical intervention.

BRIEF DESCRIPTION OF THE DRAWINGS

The above and other aspects, features and advantages of the present invention will be more apparent from the following more particular description thereof, presented in conjunction with the following drawings wherein:

FIG. 1A is a sectional view of the electrode array of FIG. 1 taken along the line A—A of FIG. 1;

FIG. 1B is a partial sectional view of the electrode array of FIG. 1 taken along the line B—B of FIG. 1;

FIG. 3 shows a slitted insertion needle into which the foldable electrode array of FIG. 1 and the insertion stylet of FIG. 2 may be placed;

FIG. 4 illustrates an alternative embodiment of an implantable, foldable electrode array made in accordance with the invention;

FIG. 4A is a sectional view of the electrode array of FIG. 4 taken through the line A—A in FIG. 4;

FIG. 5 shows the manner in which the electrode array of FIG. 4 is folded in order to fit within the lumen of an insertion tool;

FIG. 6 illustrates the folded electrode array of FIGS. 4 and 5 inside of the lumen of the insertion tool.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
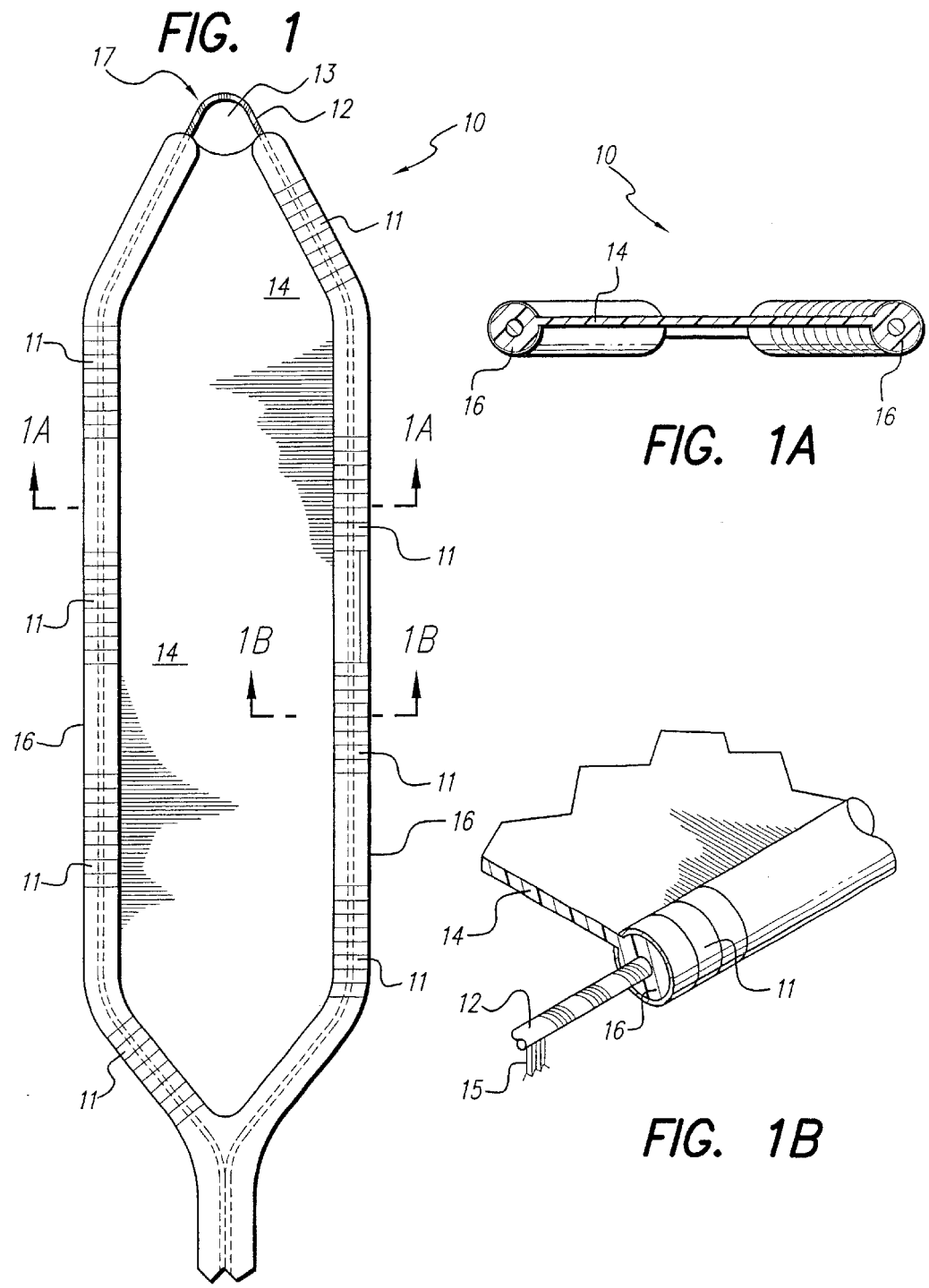
FIG. 1 shows a planar view of an implantable, foldable, collapsible electrode array made in accordance with one embodiment of the invention.

Referring first to FIGS. 1, 1A and 1B, there is shown respectively a planar view of one embodiment of an implantable, foldable, collapsible electrode array 10 made in accordance with the invention, a sectional view of the electrode array 10 taken along the line A—A, and a partial sectional view of the electrode array 10 taken along the line B—B. As can be seen in these figures, the electrode array 10 is made in the form of a silicone paddle having a number of electrode contacts 11 arranged along a cylindrical edge portion 16 of the electrode array 10. The electrode contacts 11 are spaced apart from each other, and each is electrically connected to a conductive wire(s) 15 that passes through, or is embedded within, the cylindrical edge portion 16 of the array 10.

The electrode contacts 11 may be made, e.g., from a coiled metal foil or clamped as C-shaped metal preforms. As seen best in FIG. 1B, the wires 15 that are electrically connected to the electrode contacts 11 are typically wound around a shape-memory element 12 that passes through the center of the cylindrical edge portions 16 of the array 10.

As indicated, the memory element 12 is placed in the center of the cylindrical edge portion 16. This memory element is selected to have a shape that maintains the open, paddle shape of the electrode array 10 as shown in FIG. 1. The shape-memory element 12 may be made from either metal or from a polymer, such as nylon, the memory element 12 is flexible or resilient, so that it can be folded or bent to another shape, as desired or needed, but in the absence of an external folding or bending force, assumes the open, paddle shape shown in FIG. 1.

The space between the cylindrical edge portions 16 of the paddle array 10 is filled with a thin silicone web or membrane 14. Such membrane advantageously prevents tissue ingrowth within the electrode array 10 after implant, thereby making it possible (when needed) to explant the electrode, or to reposition the electrode with minimal trauma to the patient.

At a distal tip 17 of the array 10, the thin membrane 14 and the cylindrical edge portions 16 terminate so as to expose the memory shape element 12 at the distal tip, thereby forming an attachment loop 13. This attachment loop 13 is used during the implant operation of the electrode as explained more fully below.

In one embodiment of the invention, the width of the paddle electrode array 10 of the type shown in FIG. 1, when maintained in its extended or full paddle shape as shown in FIG. 1, is approximately 10 mm, and has a length of about 45 mm. The diameter of the cylindrical edge portions is approximately 1.2 mm, and the thickness of the membrane 14 is about 0.2 mm.

Figure 2:
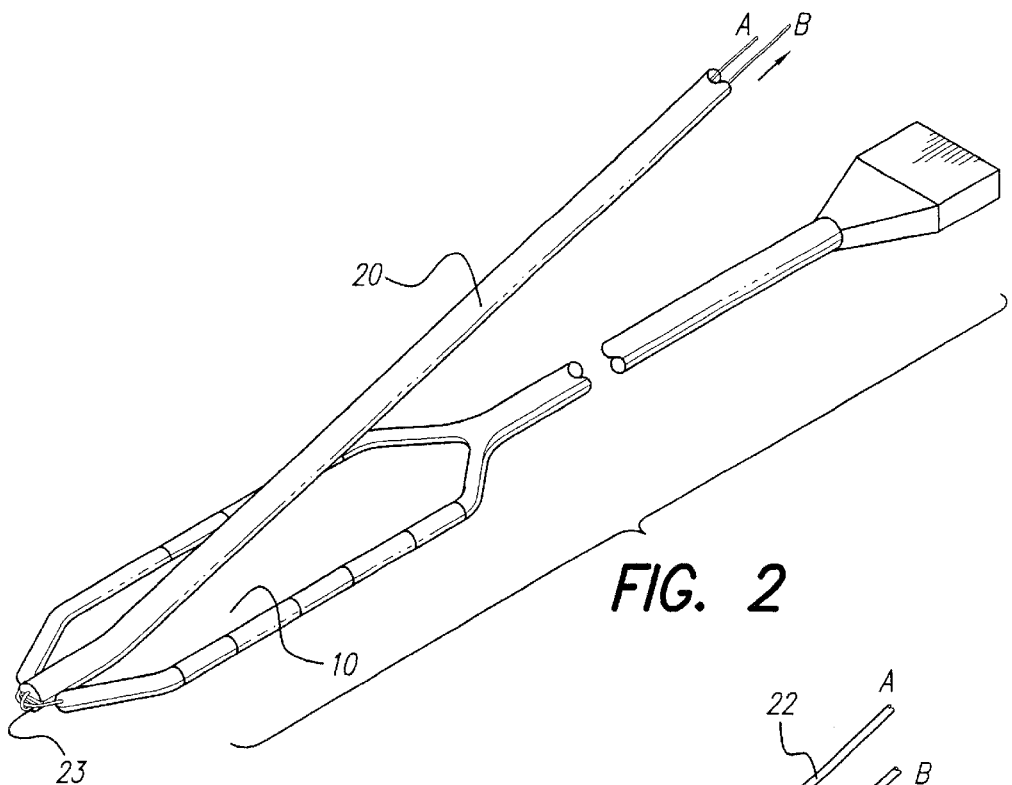
FIG. 2 illustrates one manner in which the electrode array of FIG. 1 may be implanted using an insertion stylet.
Figure 2A:
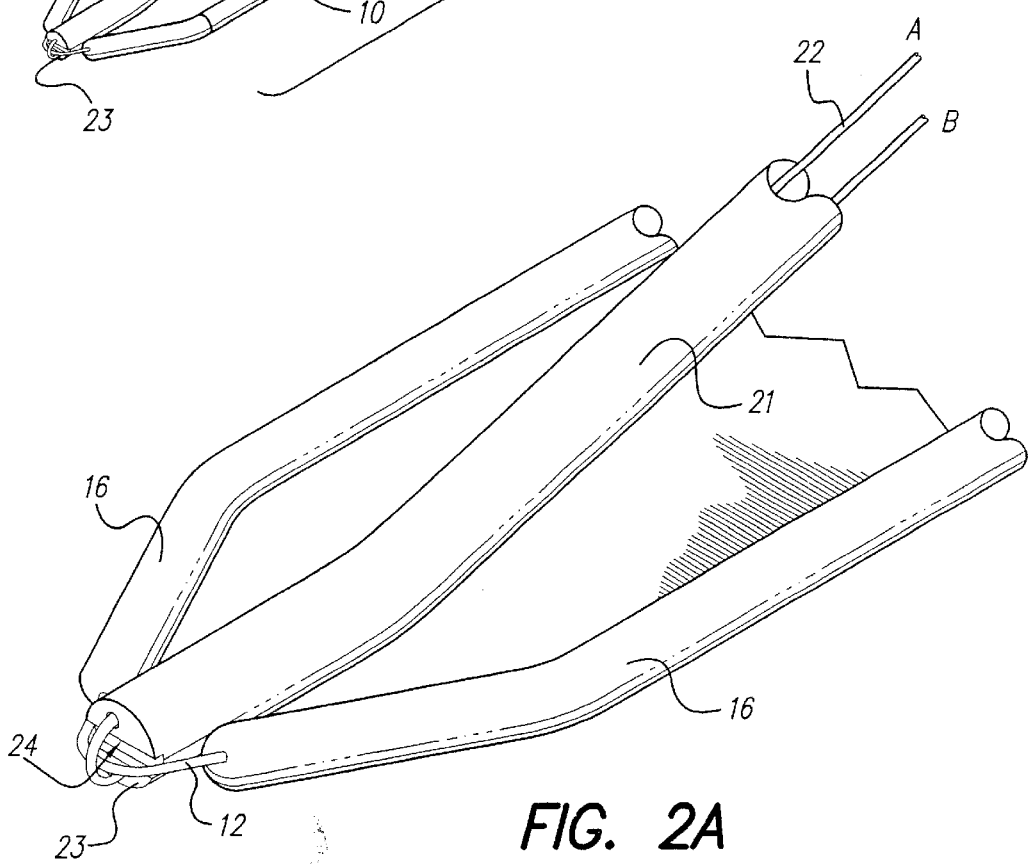
FIG. 2A depicts the manner in which the distal tip of the electrode array of FIG. 1 is held by the distal tip of the insertion stylet of FIG. 2 during the implantation process.
Figure 2B:
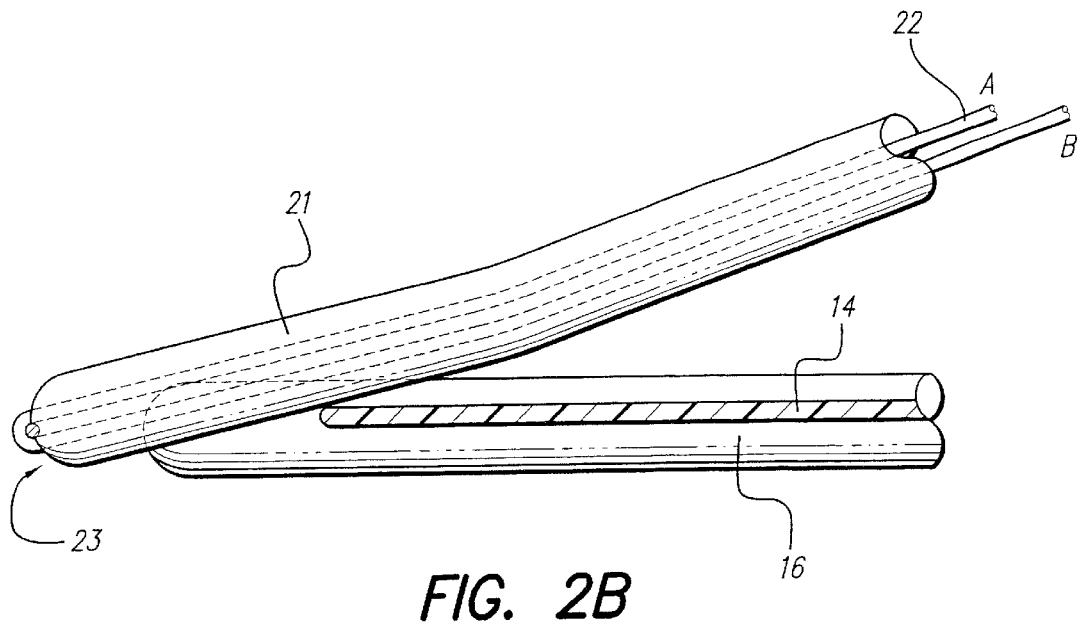
FIG. 2B is a side schematic diagram that illustrates the manner in which a releasable holding string may be threaded through the insertion stylet in order to hold the distal tip of the electrode array in a desired position within a groove of the insertion stylet during the implantation process.

The electrode array 10 includes an insertion tool 20, as shown in FIGS. 2, 2A and 2B. This insertion tool 20 may also be referred to as an insertion stylet 20.

In one embodiment, the insertion tool 20 is made from a tube 21 and holding string 22. A distal tip 23 of the insertion tool 20 may include a groove or slot 24 into which the memory element 12 may be inserted at the attachment loop 13 of the array 10. The string 22 is threaded through the tube 21 to the distal tip 23, where it wraps around (½ turn) the memory element 12, and is then threaded back through the tube 21. Thus, the two ends of the string 22, labeled "A" and "B" in the figures, exit from the proximal end of the tube 21. The diameter of the tube is typically about the same as the diameter of the cylindrical edge portions 16 of the array 10, e.g., about 1.2 mm.

Figure 3A:
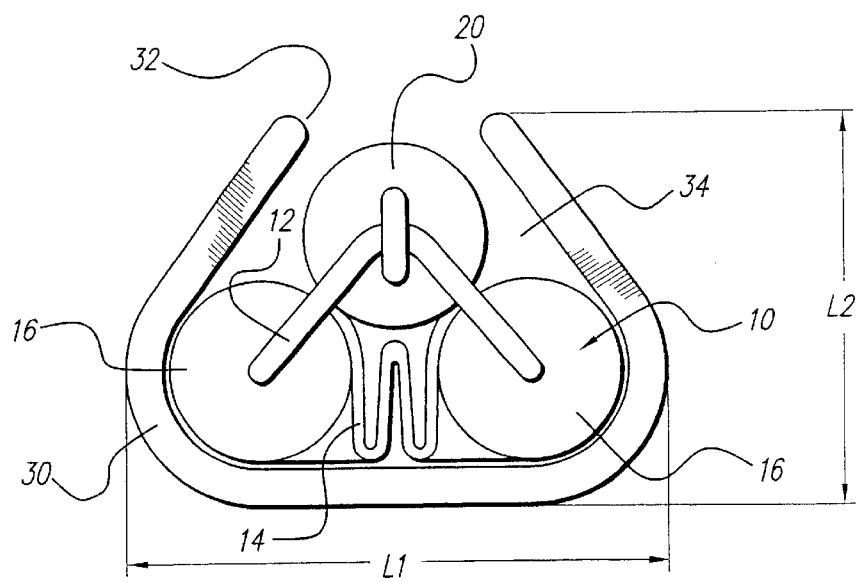
FIG. 3A depicts the manner in which the folded electrode array and insertion stylet fit within the lumen of the needle of FIG. 3.

In order to implant the electrode array 10 with the insertion stylet 20, both the electrode array 10 and insertion stylet 20 are placed within a needle 30, as shown in FIGS. 3 and 3A. The needle 30 has a longitudinal slit 32 that opens up one side thereof along its entire length. The needle 30 has a sharp distal tip 33 to facilitate its insertion into living tissue. The needle 30 is hollow, having a lumen 34 (or open channel) in the center thereof. The electrode 10 and insertion tool 20 are configured (folded or compressed) to fit within this lumen 34, as illustrated in FIG. 3A. During this configuration (folding) process, the thin membrane 14 folds against itself so that the two perimeter edge portions 16 of the array 10 and the insertion tool 20 are all held in close proximity to each other.

The needle 30 has approximate dimensions of L1 by L2 (e.g., 4.0 mm by 3.0 mm), as shown in FIG. 3A. The slit 32 has a width of about 1.2 mm, the width of the cylindrical edge portions of the lead 10, and also the width of the tube 21 that forms part of the insertion tool 21.

In order to implant the electrode array, the needle 30 with electrode array 10 and insertion tool 20 inside, is inserted into the spinal cord cavity. The insertion tool 20 is then pushed so as to eject the electrode array 10 from the lumen 34 of the needle 30 into the spinal cord cavity. Once ejected from the lumen of the needle in this manner, the memory element 12 (FIG. 1) deploys the electrode paddle array 10 from its folded position, as shown in FIG. 3A to its flat paddle shape, as shown in FIG. 1.

Once thus deployed, the insertion tool 20 may be further pushed, and/or the electrode lead may be pulled, so as to manipulate the electrode array within the spinal cord cavity to rest in an optimum or desired position. The needle 30 is then removed from the body, and the electrode lead is released through the slot or slit 32 in the needle. The string 22 is then pulled from either the "A" or "B" end in order to release the electrode array 10 from the insertion tool 20. The insertion tool 20 is then also pulled out of the tissue.

An alternative embodiment of a percutaneously implanted expandable lead/electrode array 40 made in accordance with the present invention is depicted in FIGS. 4, 4A, 5, 6 and 7.

In accordance with such alternative embodiment, there are two or more rows 42 of spaced-apart electrode contacts connected together with a thin webbing 44 and tapering into a single lead 46. In FIG. 4, three such rows, 42a, 42b and 42c, are shown. Each row of spaced-apart electrodes comprises a finger substrate made, e.g., from a suitable flexible non-conductive material such as silicone or other implantable lead materials, as is known in the art. Each finger substrate has a plurality of electrode contacts 48 exposed on the surface thereof. Each electrode contact 48 is, in turn, connected electrically with a wire (not shown) embedded within the row 42 and lead 46, thereby facilitating making electrical connection with each electrode. Any suitable implantable conductive material may be used for the electrode contacts 48.

In one particular embodiment of the electrode array 40, each electrode contact has a length of about 2 mm, and each finger of the array has an active length (where the active length is the length from the most proximal electrode contact to the most distal electrode contact) of about 10 mm. As seen in FIG. 4A, the webbing 44 has a thickness of about 0.2 mm. Each finger has a cross section having a width of about 1.75 mm and a height of about 0.80 mm. The width of the webbing 44 between adjacent fingers is approximately 0.75 mm.

In order to implant the electrode array 40, the array 40 is inserted into an insertion tool 50 as shown in FIGS. 5 and 6. As the array 40 is inserted into the implant tool 50, the fingers 42a, 42b and 42c (or however many rows or fingers there are) collapse and fold over each other. The fingers or rows 42 may be tapered so that a distal end is somewhat smaller than the proximal end.

The electrode contacts 48 on the surface of each finger 42 are preferably offset from the location of electrode contacts of an adjacent finger or row. Such offsetting of the electrode contacts facilitates the folding of one row before the next. The electrode array 40 in its folded state is shown within the insertion tool 50 in FIG. 6.

Figure 7:
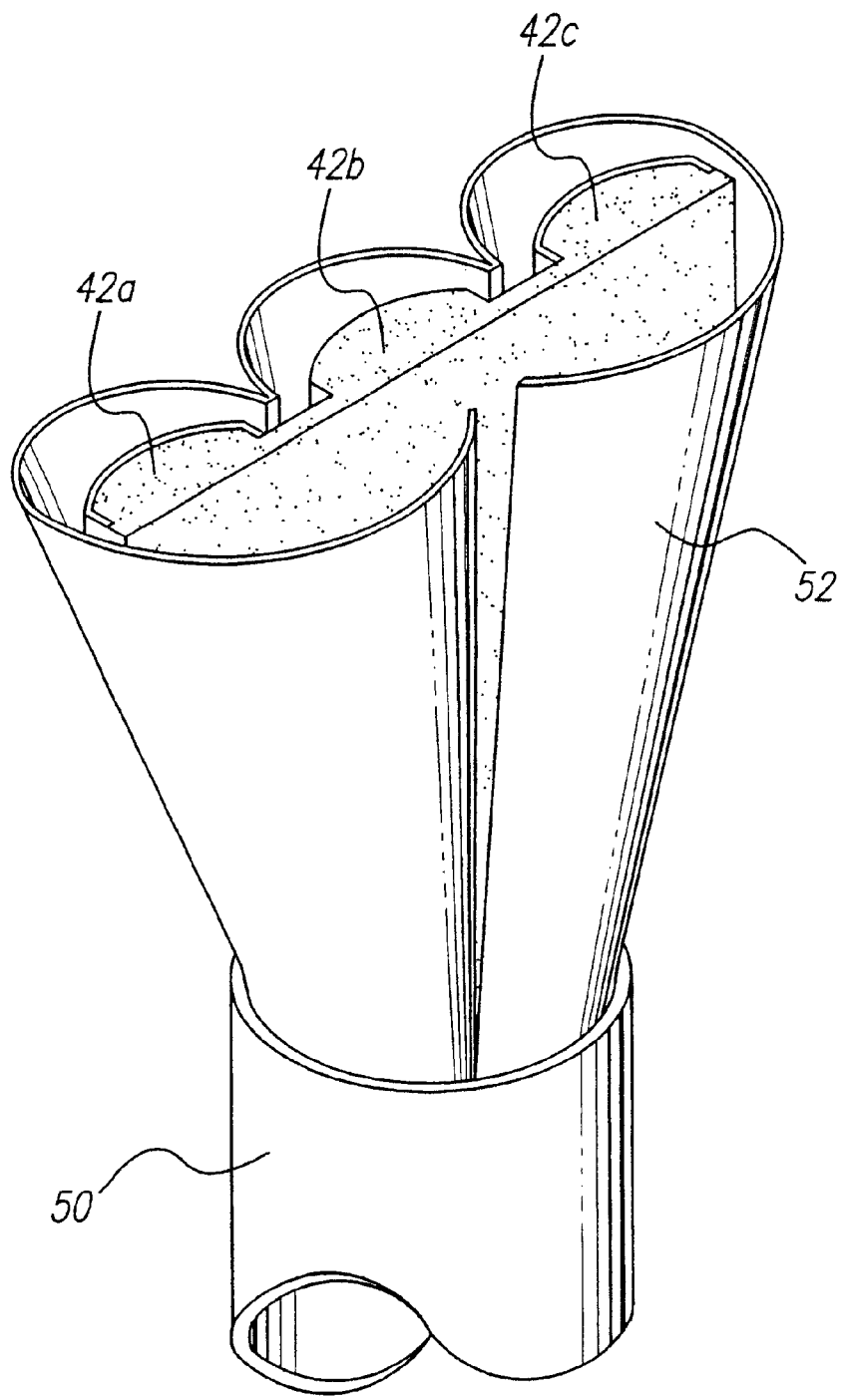
FIG. 7 depicts a loading tool that may be used in conjunction with the insertion tool in order to facilitate the folding and insertion of the electrode array of FIG. 4 into the lumen of the insertion tool.

For some implantations, it may be helpful to employ a funnel loading attachment tool 52 as illustrated in FIG. 7. With such loading tool 52, which attaches to one end of the insertion tool 50, the lead cable 46 is first inserted through the funnel tool 52 and insertion tool 50, and as this lead 46 is pulled through the tool 50, the funnel shape of the loading tool 52 automatically causes the various fingers or rows 42a, 42b, 42c to collapse and fold over each other as they are pulled into the insertion tool 50.

As described above, it is thus seen that the present invention provides a foldable, paddle-type electrode which can be implanted using a simple, needle-type tool without major surgical intervention.

As further described above, it is seen that the invention provides a loading tool that assists with the folding and inserting of the paddle-type electrode into an insertion tool.

While the invention herein disclosed has been described by means of specific embodiments and applications thereof, numerous modifications and variations could be made thereto by those skilled in the art without departing from the scope of the invention set forth in the claims.

What is claimed is:

1. An insertion needle for percutaneously implanting a foldable or compressible paddle electrode array, the insertion needle having a lumen that passes longitudinally therethrough, the lumen having a non-circular cross-sectional shape, the non-circular cross-sectional shape being adapted to receive the foldable or compressible paddle electrode array while in a folded or compressed state.

2. The insertion needle of claim 1 wherein the lumen has a width L1 and a height L2, and wherein L2 is greater than L1.

3. The insertion needle of claim 2 wherein L2 is about 4 mm and L1 is about 3 mm.

4. The insertion needle of claim 2 wherein the insertion needle further includes a sharp distal tip to facilitate its insertion into living tissue.

5. An insertion needle for use with an implantable, expandable, multicontact electrode, the insertion needle comprising
a hollow needle having a channel passing through the center thereof;
wherein the hollow needle has a sharp distal tip, and
wherein the hollow needle further has a longitudinal slit that opens up one side of the channel, and
wherein the channel has a non-circular cross-sectional shape adapted to receive the implantable, expandable, multicontact electrode while in a folded or compressed state.

6. The insertion needle of claim 5 wherein the non-circular cross-sectional shape is further adapted to receive an insertion stylet along with the folded or compressed implantable, expandable, multicontact electrode.

7. The insertion needle of claim 5 wherein the channel has approximate dimensions of L1 by L2, where L1 is greater than L2.

8. The insertion needle of claim 7 wherein L1 is approximately 4 mm and L2 is approximately 3 mm.

9. The insertion needle of claim 8 wherein the slit has a width of about 1.2 mm.

10. An insertion needle through which a paddle electrode array may be percutaneously implanted into living tissue, the insertion needle having a lumen that passes therethrough, the lumen having a non-circular cross-sectional shape, wherein the lumen has a width L1 and a height L2, and wherein L1 is greater than L2.

11. The insertion needle of claim 10 wherein L1 is about 4 mm and L2 is about 3 mm.

12. The insertion needle of claim 10 wherein the insertion needle further includes a sharp distal tip to facilitate its insertion into living tissue.

13. The insertion needle of claim 10 further including a longitudinal slit that opens up one side of the lumen.

14. The insertion needle of claim 13 wherein the longitudinal slit has a width of about 1.2 mm.

* * * * *